(12) United States Patent
Cwik et al.

(10) Patent No.: US 6,271,526 B1
(45) Date of Patent: Aug. 7, 2001

(54) EFFICIENT RADIATION COUPLING TO QUANTUM-WELL RADIATION-SENSING ARRAY VIA EVANESCENT WAVES

(75) Inventors: Thomas Cwik, Altadena; Cavour Yeh, Los Angeles, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/418,451

(22) Filed: Oct. 15, 1999

Related U.S. Application Data

(60) Provisional application No. 60/151,812, filed on Aug. 30, 1999, and provisional application No. 60/104,434, filed on Oct. 15, 1998.

(51) Int. Cl.[7] .................................................. H01L 29/15
(52) U.S. Cl. ............................................................ 250/371
(58) Field of Search ............................................... 250/371

(56) References Cited

U.S. PATENT DOCUMENTS

| | | | |
|---|---|---|---|
| Re. 35,215 | * 4/1996 | Waarts et al. | 372/108 |
| 4,856,017 | * 8/1989 | Ungar | 372/96 |
| 5,170,402 | 12/1992 | Ogita et al. | |
| 5,265,107 | * 11/1993 | Delfyett, Jr. | 372/11 |
| 5,351,127 | * 9/1994 | King et al. | 356/445 |
| 5,642,375 | * 6/1997 | King et al. | 372/97 |
| 5,644,584 | * 7/1997 | Nam et al. | 372/20 |
| 5,973,727 | * 10/1999 | McGrew et al. | 348/41 |
| 6,088,377 | * 7/2000 | Matsuda | 372/50 |

OTHER PUBLICATIONS

IEEE Transactions On Microwavy Theory and Techniques, vol. MTT–16, No. 12, pp. 1048–1054, Dec. 1968, R. Shubert and J. H. Harris, "Optical Surface Waves On Thin Films And Their Application To Integrated Data Processors".

Applied Optics, vol. 10, pp. 12–30, Nov. 1971, P. K. Tien, "Light Waves In Thin Films and Integrated Optics".

IEEE Transactions On Antennas and Propogation, vol. 40, No. 12, pp. 1496–1504, Dec. 1992, Tom Cwik, "Coupling Finite Element and Integral Equation Solutions Using Decoupled Boundary Meshes".

* cited by examiner

*Primary Examiner*—Constantine Hannaher
*Assistant Examiner*—Otilia Gabor
(74) *Attorney, Agent, or Firm*—Fish & Richardson P.C.

(57) ABSTRACT

Devices and techniques for using a prism to couple IR radiation to a quantum-well sensor with a polarization substantially perpendicular to the quantum-well layers.

19 Claims, 5 Drawing Sheets

EFFICIENT RADIATION COUPLING TO QUANTUM-WELL RADIATION-SENSING ARRAY VIA EVANESCENT WAVES

This application claims the benefit of U.S. Provisional Application Nos. 60/104,434, filed on Oct. 15, 1998, and 60/151,812, filed on Aug. 30, 1999.

ORIGIN

The devices and techniques described herein were made in the performance of work under a NASA contract, and is subject to the provisions of Public Law 96-517 (35 U.S.C. §202) in which the Contractor has elected to retain title.

BACKGROUND

This specification relates to devices and techniques of coupling radiation energy to a light sensing array, and more particularly, to radiation coupling to a quantum-well infrared sensing array via evanescent waves.

Quantum-well semiconductor devices can be designed to respond to radiation energy to produce charge indicative of the amount of received radiation. The radiation-induced charge can then be converted into an electrical signal (e.g., a voltage or current) to be processed by signal processing circuitry. Many quantum-well devices use an intraband transition between a ground state and an excited state in the same band (i.e., a conduction band or a valance band) of the quantum-well structure to detect infrared ("IR") radiation. The compositions of lattice-matched semiconductor materials of the quantum well layers can be adjusted to cover a wide range of wavelengths for infrared detection and sensing. In comparison with other radiation detectors, quantum-well structures can achieve a high quantum efficiency, a low dark current, compact size and other advantages. Infrared quantum-well sensing arrays may be used for various applications, including night vision, navigation, flight control, environmental monitoring.

A quantum well infrared sensor only responds to incident radiation with a polarization that is perpendicular to the plane of the quantum well layers. This is because only this polarization can induce an intraband transition at a desired infrared wavelength. Hence, the direction of the electric field of the received radiation must be parallel to the growth direction of the quantum well layers. One direct approach for light coupling is to orient the quantum well infrared photodetector at an angle to the incident infrared radiation (e.g., forty-five degree). The incident electric field will have a component along the growth direction of the quantum well layers to produce absorption of photons. Any additional scattering can enhance this absorption.

For applications based on imaging at focal plane arrays, the photodetector array is often oriented perpendicular to the scene to be imaged. Since the electric vector is essentially parallel to the quantum well layers in this arrangement, the quantum well layers absorb little or no light. One way to provide proper coupling is to use a random surface to scatter the incident radiation into the correct polarization for absorption. Alternatively, grating couplers with one or two-dimensional periodic profiles can be used to convert normally-incident radiation to waves propagating parallel to the quantum well layers.

SUMMARY

The present disclosure includes techniques and devices that couple radiation to quantum-well sensors via evanescent waves so that the polarization of the coupled energy is substantially perpendicular to the quantum-well layers. Efficient IR coupling can be achieved in various applications.

One embodiment of a semiconductor device includes substrate, a quantum-well sensing region in the substrate, a non-sensing region in the substrate, and a prism engaged to the substrate. The sensing region has a quantum-well structure of alternating semiconductor layers parallel to the substrate to absorb radiation at or near a resonance wavelength. The non-sensing region at least partially encloses the sensing region to form a resonant optical cavity whose optic axis is parallel to said substrate.

The prism includes a flat surface and a slanted surface that forms an angle with the flat surface. The flat surface is substantially parallel to and spaced from the substrate by an air gap less than one wavelength of the radiation to permit evanescent coupling to the sensing region. The angle of the slanted surface is configured to couple radiation to the flat surface at an incident angle that is equal to or greater than a critical incident angle so that a total internal reflection occurs at the flat surface.

This configuration produces an evanescent wave that propagates along the flat surface. When the beam incident to the flat surface includes a polarization in the incident plane, the evanescent wave has a polarization perpendicular to the flat surface and hence the quantum well layers. Under this condition, the radiation energy in the evanescent wave can be absorbed by the quantum-well layers.

The resonance peak of the optical cavity may substantially overlap with said resonance wavelength of said sensing region in order to efficiently absorb the radiation. The air gap between the prism and the substrate may be filled with a dielectric material which has an index of refraction less than that of the prism.

These and other aspects and associated advantages will become more apparent in light of the detailed description, the accompanying drawings, and the appended claims.

DETAILED DESCRIPTION

A radiation beam traveling in a first medium towards an interface with a second medium may generally undergo both reflection where a portion of the incident energy is reflected back to the first medium and refraction where a portion of the incident energy is refracted into a refracted wave in the second medium. A special effect occurs when (1) the index of refraction of the first medium, $n_1$, is greater than that of the second medium, $n_2$, and (2) the incident angle is equal to or greater than the critical incident angle $\theta_c = \sin^{-1}(n_2/n_1)$. Under these conditions, the refracted wave is an evanescent wave that propagates along the interface and decays exponentially within the second medium. Hence, in the absence of other energy coupling mechanisms, the incident energy does not propagate into the second medium and therefore is "totally" reflected back into the first medium. For this reason, the above effect is often referred to as "total internal reflection."

The reflection would not be "total" under the above conditions, if an additional energy coupling mechanism can be implemented to extract the energy from the evanescent wave at the interface. The present disclosure includes techniques and devices to purposefully direct the incident IR energy to satisfy the total reflection conditions so that quantum-well IR sensors near the interface can be used to absorb the energy in the evanescent wave to detect the incident radiation. This is possible because the polarization of the evanescent wave is perpendicular to the interface. Hence, the quantum-well IR sensors can be oriented to have their quantum layers substantially parallel to the interface to satisfy the requirement for absorption. A radiation-coupling prism can be implemented to provide the interface so that quantum-well IR sensor array can be used in the focal plane of an imaging system. This prism coupling mechanism not only offers an alternative technology to coupling techniques that use a scattering random surface or a diffraction grating but also provides significant advantages over previous coupling techniques in coupling efficiency and other aspects of quantum-well IR sensor arrays.

Figure 1A:
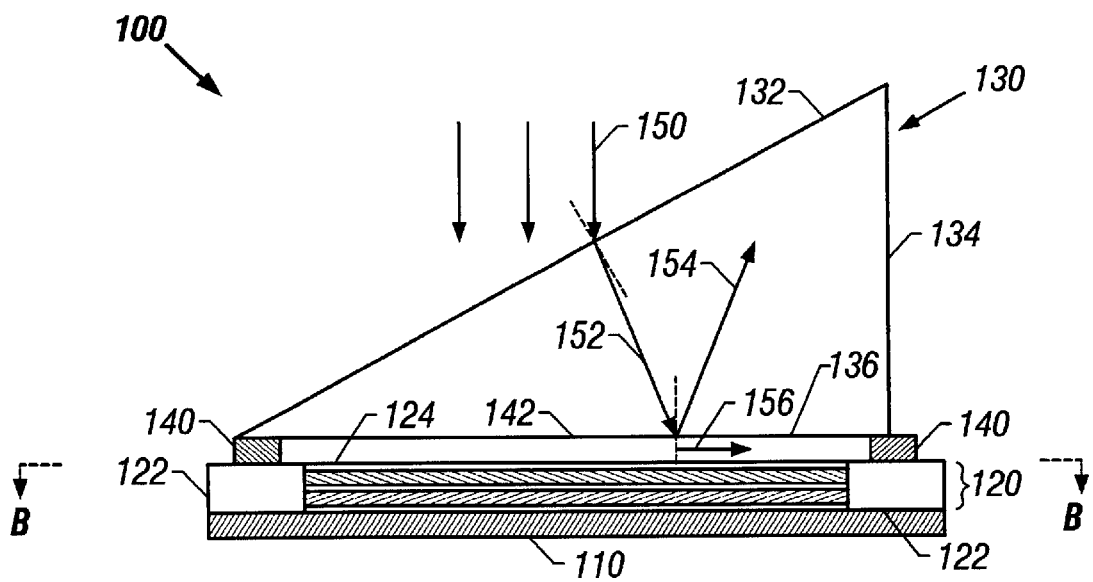
FIGS. 1A and 1B show a prism-coupled quantum-well IR sensor according to one embodiment of the present disclosure.
Figure 1B:
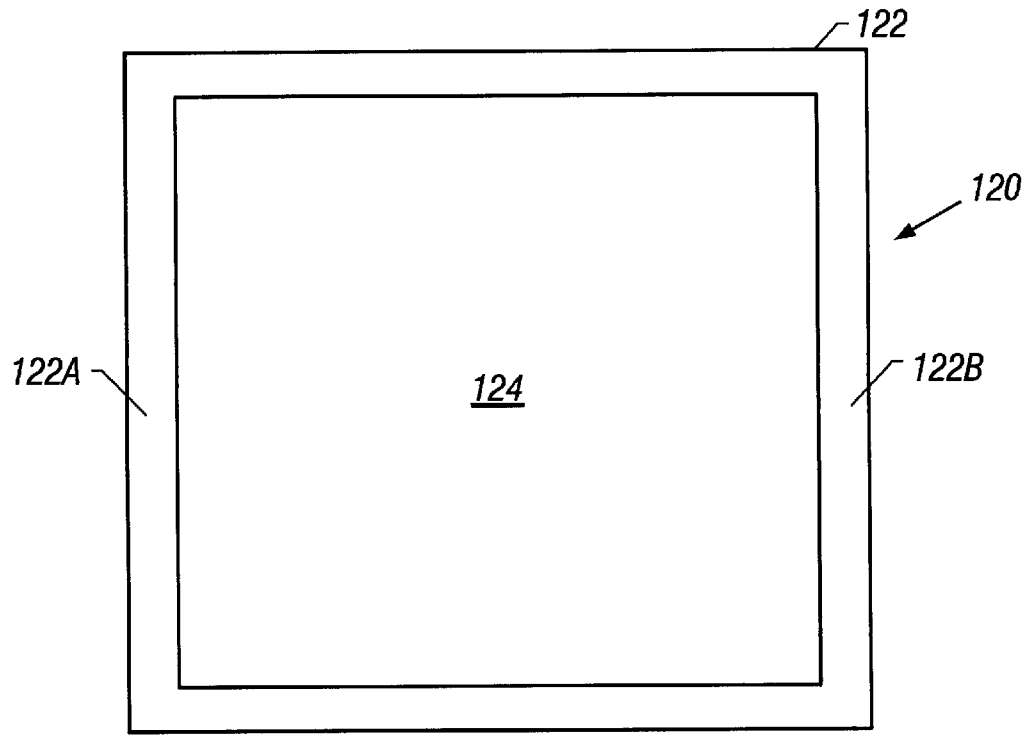

FIGS. 1A and 1B show one embodiment of a prism-coupled quantum-well IR sensing device 100. This device 100 represents a single sensor and may also represent one sensing pixel of a monolithic array of sensing pixels formed on a substrate. A semiconductor substrate 120 is processed to include at least two separate regions: a non-sensing region 122 and a quantum-well IR sensor region 124. The quantum-well IR sensor region 124 includes alternating active and barrier semiconductor layers to absorb IR radiation at or near a selected resonance IR wavelength. Examples of such quantum-well structures include, among others, $Al_xGa_{1-x}As$ (barrier)/GaAs(active layer) and $Ga_xIn_{1-x}P$ (barrier) /InP (active layer). The quantum-well layers in the region 124 are parallel to the outer surfaces of the substrate 120. A metallic layer 110 is formed in contact with one side of the substrate 120 to serve as an electrode which provides a desired electrical bias to the quantum-well region 124. Another electrode (not shown) is formed on the opposite side of the quantum-well region 124 and is set at a different electrical potential from that of the metallic layer 110.

The non-sensing region 122 is designed to at least in part enclose the region 124 and hence form a resonant optical cavity. In an array sensor where the region 124 represents one of many sensing pixels, the non-sensing region 122 also serves to isolate adjacent sensing pixels. Two subregions 122A and 122B of the region 122 may be located in opposite sides of the region 124 so that the optic axis of the cavity is along the quantum-well layers. Since the material compositions of the regions 122 and 124 are different, their indices of refractions are also different so as to cause optical reflection at an interface between the regions 122 and 124. Such optical reflection creates optical feedback in the quantum well region 124 to form resonant cavity modes.

A prism 130 is positioned over the quantum-well region 124 to receive an incident beam and is designed to provide evanescent coupling to the quantum-well region 124 when an incident beam is generally incident at a direction substantially perpendicular to the substrate 120. The prism 130 includes a slanted surface 132 that receives the incident radiation, a surface 134 that is substantially perpendicular to the substrate 120, and a bottom flat surface 136 that is adjacent to the quantum-well region 124 for evanescently coupling incident energy. A spacer 140, which may be made of a dielectric material such as a semiconductor compound, is formed over the substrate 120 to support the prism 130 so that the prism surface 136 is spaced from the quantum-well region 124 by an air gap 142 less than one wavelength of the incident energy. Since the index of the prism 130 is greater than that of the air, an evanescent refracted wave 156 can be generated to propagate along the surface 136 when an incident beam 152 directed from the slanted surface 132 has an incidence angle at the surface 136 that is greater than the critical angle $\theta_c$.

The angle between the slanted surface 132 and the surface 136 is designed to allow a generally-normal incident beam 150 to be refracted at the surface 132 to produce the above refracted wave 152. Although a portion of the beam 152 is reflected back to the prism 130 by the surface 136, it is the energy refracted into an evanescent wave 156 that is to be detected by the quantum-well region 124. When the refracted beam 152 is at least partially polarized within the incident plane defined by its propagation direction and the normal direction of the surface 136, at least a portion of the evanescent wave 156 is polarized perpendicular to the surface 136 and hence can be absorbed by the quantum-well region 124. Depending the polarization state of the incident radiation, the relative orientation between a polarization of the incident beam 150 and a direction of the prism 130 may be adjusted, or a polarizing element (e.g., a polarization rotator) may be used, to increase or maximize the portion of light that is polarized in the incident plane. This increases the absorption efficiency by the quantum-well region 124.

Hence, the prism 130 is specifically designed to convert, through the evanescent field, a portion of the incident polarization that is parallel to the quantum-well layers into a polarization that is perpendicular to the quantum-well layers. Therefore, the radiation energy coupled into the quantum-well region 124 has the desired polarization to allow efficient absorption in the quantum well layers.

A number of device parameters can affect the efficiency of such polarization conversion. These parameters include the angle of prism 130 between surfaces 132 and 136, the indices of the prism 130, the air gap 142, and the quantum-well region 124, and thickness of the air gap 142, and the length of the coupling region. For example, to design the device 100 for sensing IR radiation at or near a selected wavelength, the optical resonance cavity formed by the region 122 may be designed to have a resonance peak at that selected wavelength with a desired linewidth. Effects of these and other parameters may be analyzed by numerically solving Maxwell equations. See, e.g., Thomas Cwik, "Coupling Finite Element and Integral Equation Solutions Using Decoupled Boundary Meshes," IEEE Transactions on Antennas and Propagation, 40, 1496–1504 (1992).

Figure 2:
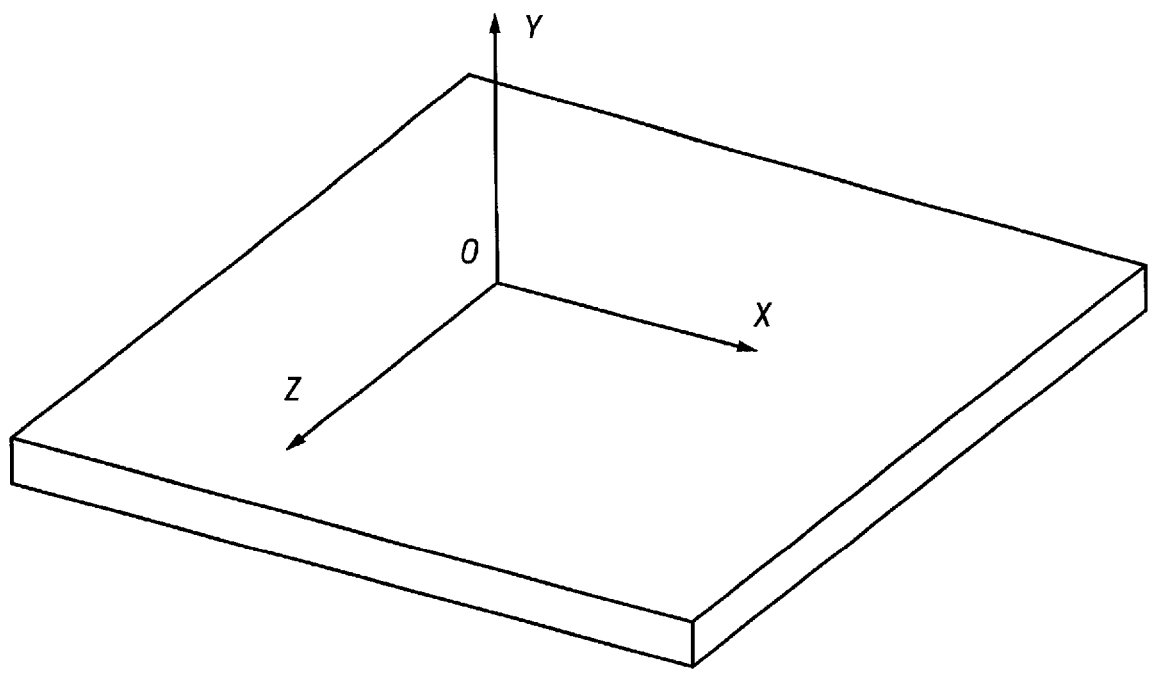
FIG. 2 shows a Cartesian coordinate system used for calculating the electric field that is perpendicular to the quantum well sensor as a function of position.

FIG. 2 shows a Cartesian system that is used for this numerical analysis, where x and z axes are in the side of the quantum-well region 124 that is in contact with the metallic layer 110, and the y axis is perpendicular to the substrate 120 and is directed from the quantum-well region 124 to the prism 130. The electric field $E_y(x, y, z)$ at any location can be calculated as a function of the above and other device parameters. Then the device parameters are adjusted to achieve a desired level of $E_y(x, y, z)$ in the quantum-well region 124 for efficient sensing applications.

One way to evaluate a design of the device 100 is to determine the sum of the intensity associated with $E_y(x, y, z)$ in the quantum-well region 124. Hence, a figure of merit, F, may be defined as:

$$F(\lambda) = \int\int\int |E_y(x,y,z,\lambda)|^2 dx dy dz,$$

where $\lambda$ is the wavelength of radiation, and the integration is over the volume of the quantum-well region 124. Device parameters are selected so that F is above a desired value for a particular application.

TABLE 1

| | |
|---|---|
| Index of Prism 130 | 3.1 (GaAs) |
| Index of Air Gap 142 | 1.0 (Air) |
| Index of Quantum Well 124 | 3.1 (GaAs) |
| Length of the Prism 130 | 50 μm |
| Thickness of Air Gap 142 | 3.75 μm |
| Thickness of Quantum Well 124 | 1.875 μm |
| Angle of Prism | 27.34° |

Figure 3:
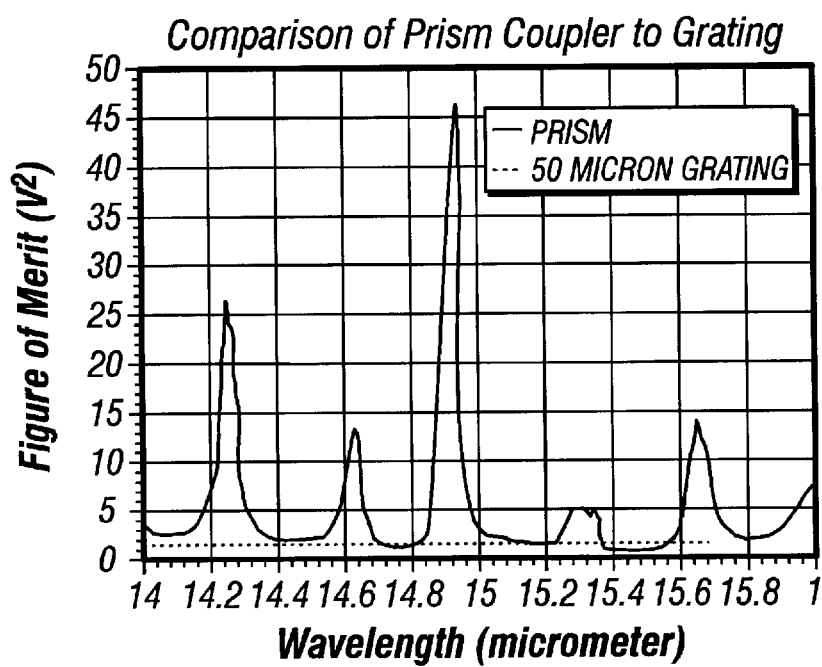
FIG. 3 shows calculated total power of the polarization that is perpendicular to the quantum-well layers over a given area of the quantum well sensing area for both an implementation of FIG. 1A and a grating-coupled quantum-well IR sensor.

FIG. 3 shows the figure of merit of one implementation of the device 100 as a function of the incident wavelength. The parameters are listed in TABLE 1. As the incident wavelength changes from about 14 μm to about 16 μm, the figure of merit undergoes a periodic change due to the resonant cavity modes formed by the region 122. The figure of merit reaches a maximum value when the parameters overlap a strong intraband transition with a resonance cavity mode, e.g., the mode at 14.95 μm. The numerical analysis suggests that, unlike a conventional optical cavity, the resonant modes of the cavity formed by the region 122 have a dependence on not only the structure of regions 122 and 124 but also on the angle of the prism 130 and the thickness values of the air gap 142 and the quantum-well region 124. Hence, the position of the highest peak can be adjusted to a desired position by selecting a desired combination of device parameters.

As a comparison, FIG. 3 also shows the figure of merit for a quantum-well IR device using a 50-μm grating for coupling. The grating has 10 periods. The active quantum-well region is a rectangle of 50 μm by 3.75 μm. The coupling efficiency of the grating is many times smaller than that of the evanescent coupling by a properly designed prism coupler.

Figure 4A:
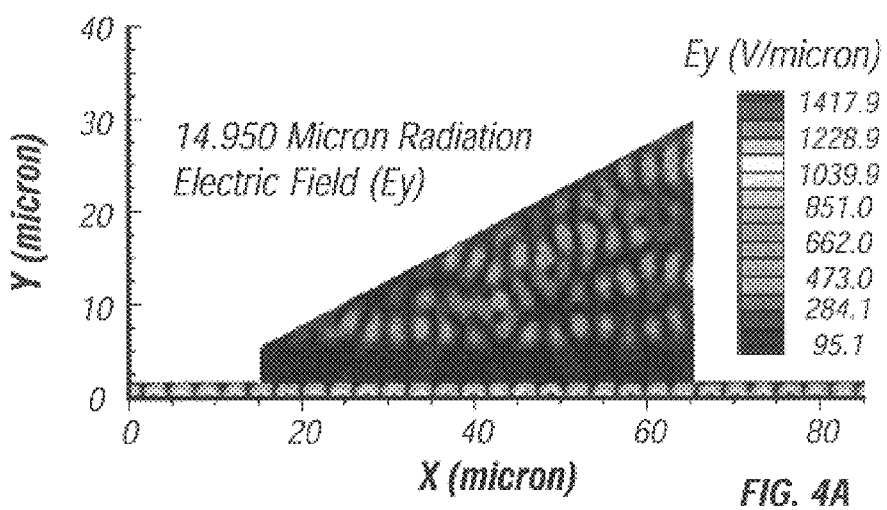
FIGS. 4A, 4B, and 4C show spatial distribution of the electric field perpendicular to the quantum layers in a device based on the embodiment in FIG. 1A.
Figure 4B:
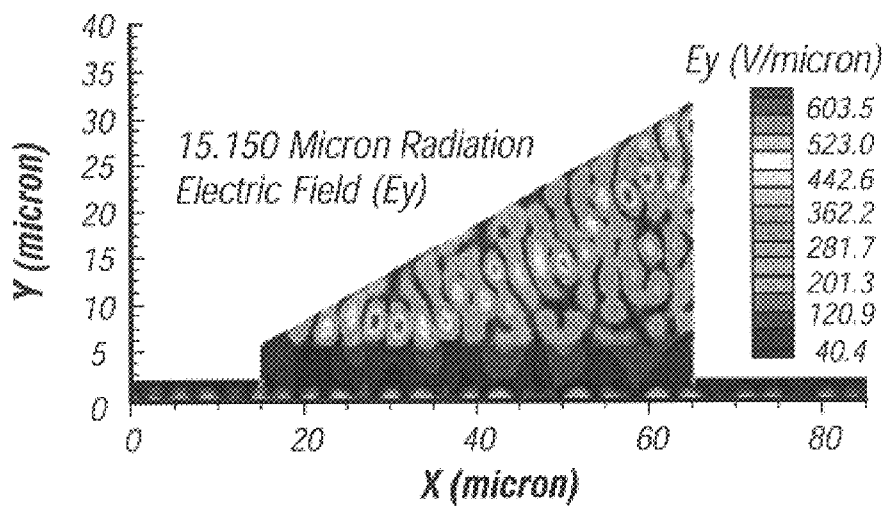
Figure 4C:
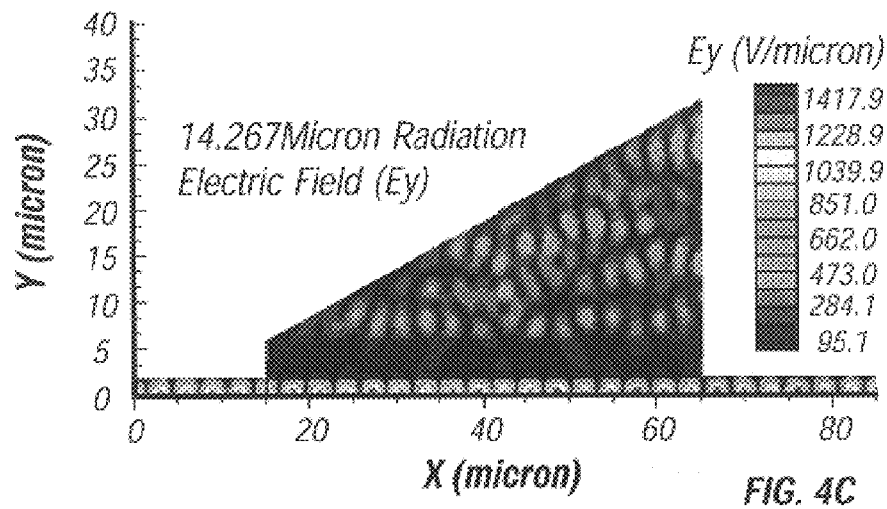

FIGS. 4A, 4B, and 4C further show the spatial distribution of the $E_y(x, y, z, \lambda)$ inside the quantum-well region 124 and the prism 130 at three different incident wavelengths (14.950 μm, 15.150 μm, and 14.267 μm) for the device 100 according to Table 1. When the incident radiation is at 14.950 μm, according to FIG. 3, the figure of merit is at a maximum indicating that most of the incident parallel polarized field has been transformed to vertically polarized field inside the quantum well layer. Hence, as expected, FIG. 4A shows concentration of high magnitude $E_y$ field inside the quantum well layer. When the incident radiation is at 15.150 μm, according to FIG. 3, the figure of merit is at a minimum indicating that only a limited amount of the incident parallel polarized field has been transformed to vertically polarized field inside the quantum well layer. Hence, only low magnitude $E_y$ is shown inside the quantum well layer, while higher magnitude $E_y$ is found inside the prism. FIG. 4C shows the $E_y$ field for the incident radiation at 14.267 μm, another resonant peak in the figure of merit in FIG. 3, which indicates good absorption by the quantum well layer. These results indicate the importance of selecting proper device parameters for a device 100 in order to achieve an optimal performance at or near an wavelength of interest.

Figure 5:
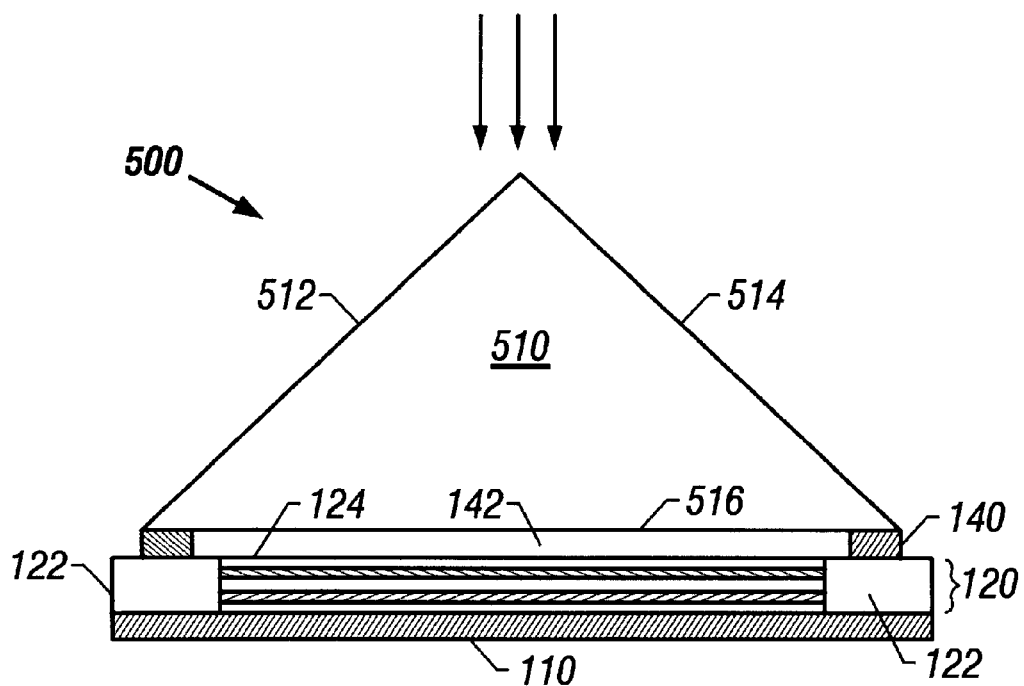
FIGS. 5, 6, and 7 show alternative embodiments of a prism-coupled quantum-well IR sensor.

FIG. 5 shows an alternative embodiment 500 where the wedge-shaped prism 130 of FIG. 1A is replaced by a pyramid-shaped prism 510. The pyramid-shaped prism 510 has two slanted surfaces 512 and 514 that refract light rays in the prism 510 so that the incident angles of refracted rays at the bottom flat surface 516 are equal to or greater than the critical angle. This design reduces the height of the prism and hence makes the device more compact.

Figure 6:
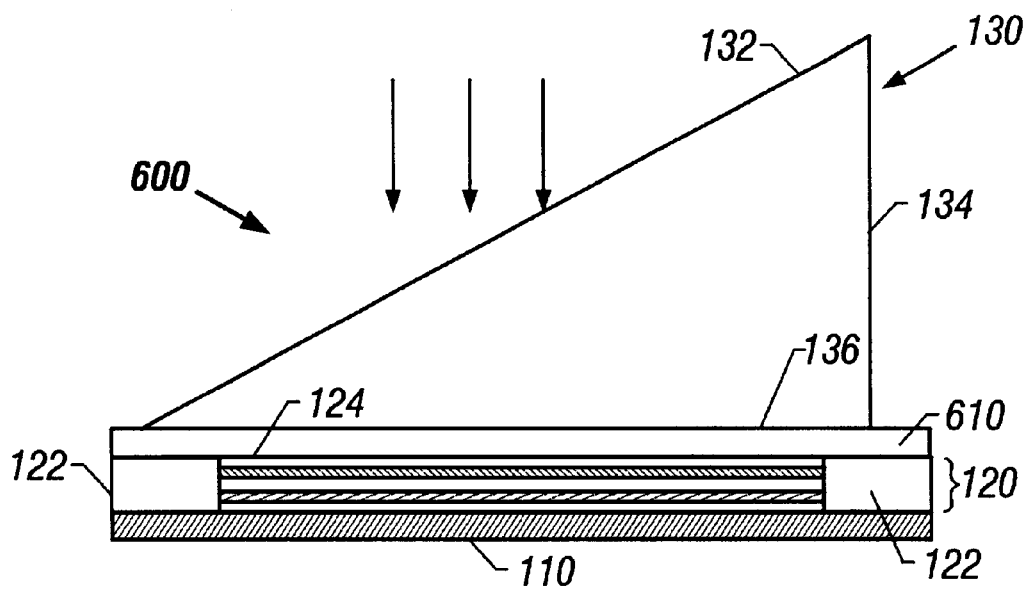
Figure 7:
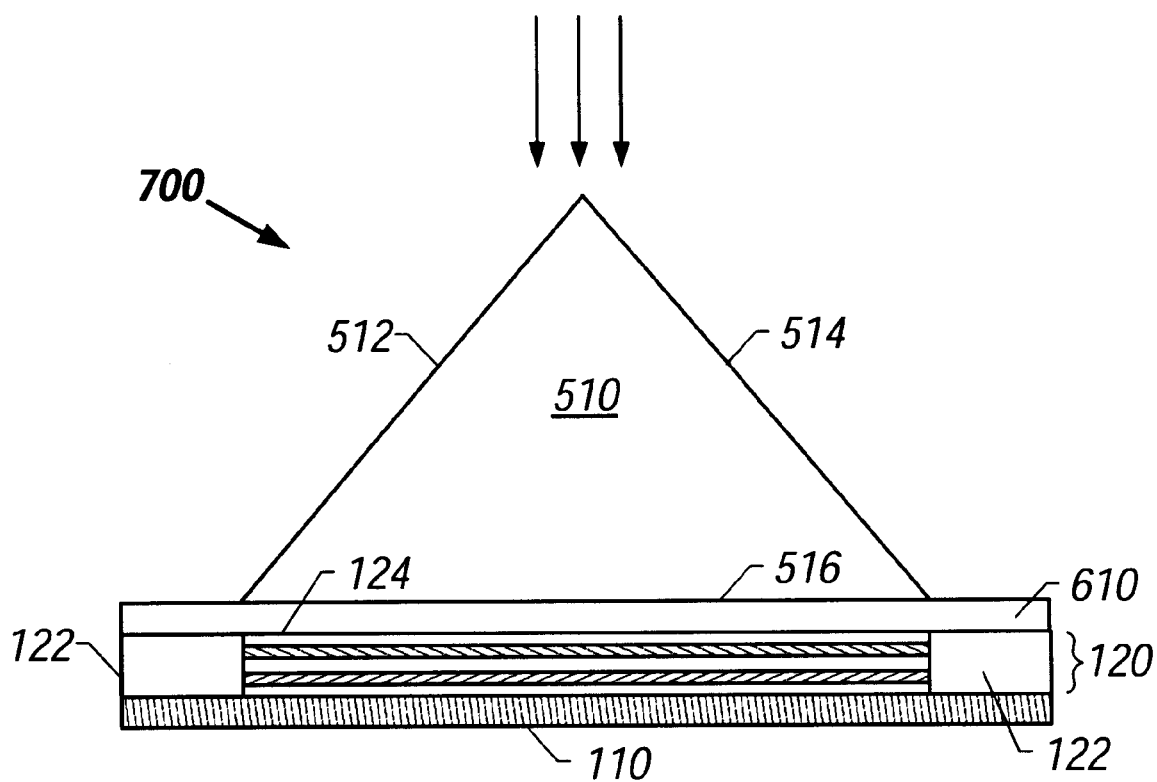

The air gap 142 may also be replaced by a dielectric spacer layer which has an index less than that of the prism. FIGS. 6 and 7 show such devices for two different types of prisms, where a dielectric layer 610 is used as a spacer between the prism (510 or 130) and the quantum-well region 124. The dielectric layer 610 may be any suitable dielectric material that can be deposited over the substrate 120 and has an index of refraction less than that of the prism 510 or 130. For example, the semiconductor material for the substrate 120 can be used to form the layer 610.

It is also desirable to form the prism 130 or 510 from a semiconductor material so that all elements in the above devices can be integrated monolithically by a sequence of wafer processing operations. This can simplify the device fabrication, reduce the cost, and facilitates integration with other devices such as signal processing circuits.

Although only a few embodiments are described, various modifications and enhancements may be made without departing from the following claims.

What is claimed is:

1. A semiconductor device, comprising:
   a semiconductor substrate having a sensing region that has a quantum-well structure of alternating semiconductor layers parallel to said substrate to absorb radiation at or near a resonance wavelength, and a non-sensing region that at least partially encloses said sensing region to form a resonant optical cavity whose optic axis is parallel to said substrate; and
   a prism engaged to said substrate over said sensing region, said prism having a flat surface substantially parallel to and spaced from said substrate by an air gap less than one wavelength of the radiation to permit evanescent coupling to said sensing region, and a slanted surface forming a desired angle with respect to said flat surface to couple radiation to said flat surface at an incident angle that is equal to or greater than a critical incident angle that would cause a total internal reflection at said flat surface,
   wherein a resonance peak of said optical cavity substantially overlaps with said resonance wavelength of said sensing region.

2. A device as in claim 1, further comprising a dielectric layer formed in said air gap between said substrate and said flat surface of said prism, said dielectric layer having an index of refraction less than an index of refraction of said prism.

3. A device as in claim 2, wherein said dielectric layer includes a semiconductor material.

4. A device as in claim 1, wherein said prism is a right-angled prism.

5. A device as in claim 1, wherein said prism has a second slanted surface that forms an angle with respect to said flat surface to couple radiation to said flat surface at an incident angle that is equal to or greater than said critical incident angle.

6. A device as in claim 5, wherein said slanted surface and said second slanted surface intercepts with each other.

7. A semiconductor device, comprising:
   a substrate formed of a semiconductor material and having a first surface and a second surface opposing said first surface;

a quantum-well sensing region in said substrate, having alternating semiconductor layers of two different compositions that are substantially parallel to said first and second surfaces and absorb radiation at or near a resonance wavelength that is polarized perpendicular to said semiconductor layers;

a non-sensing region in said substrate, having an index of refraction different from an index of refraction of said sensing region, to at least partially enclose said sensing region to form a resonant optical cavity whose optic axis is parallel to said semiconductor layers;

a conductive layer formed over said second surface to supply an electrical potential to said sensing region;

a dielectric layer formed over said first surface with a thickness less than one wavelength of the radiation; and a prism engaged to said substrate over said sensing region and comprising:

a flat surface in contact with said dielectric layer, and a slanted surface forming a desired angle with respect to said flat surface to couple radiation to said flat surface at an incident angle equal to or greater than a critical angle for a total internal reflection to cause an evanescent wave to propagate parallel to said first surface in said sensing region.

8. A device in claim 7, wherein said prism, said dielectric layer, and said sensing region are configured in a way that a resonance peak of said optical cavity substantially overlaps with said resonance wavelength of said sensing region.

9. A device as in claim 7, wherein said dielectric layer includes an air gap.

10. A device as in claim 7, wherein said dielectric layer includes a semiconductor compound.

11. A device as in claim 7, wherein said prism is a right-angled prism.

12. A device as in claim 7, wherein said prism has a second slanted surface that forms an angle with respect to said flat surface to couple radiation to said flat surface at an incident angle that is equal to or greater than said critical incident angle.

13. A device as in claim 12, wherein said slanted surface and said second slanted surface intercepts with each other.

14. A method for detecting radiation by using a semiconductor quantum-well sensor, comprising:

projecting a beam of radiation towards a quantum-well sensor in a direction substantially perpendicular to quantum-well layers;

using a first surface of a prism to receive the beam and a second surface of the prism to receive the beam from the first surface at an incident angle equal to or greater than a critical angle for a total internal reflection so as to produce an evanescent wave propagating along said second surface, wherein the beam is at least partially polarized in an incident plane that is defined by the direction of the beam and a normal direction of the second surface; and placing the quantum-well sensor near said second surface by a distance less than one wavelength of the radiation to couple radiation energy of the evanescent wave into the quantum-well sensor so that at least a portion of the evanescent wave in the quantum-well sensor is polarized perpendicular to the quantum-well layers.

15. A method as in claim 14, further comprising:

placing a dielectric layer between the quantum-well sensor and the second surface of the prism, wherein the dielectric layer has an index of refraction less than an index of refraction of the prism.

16. A method as in claim 14, further comprising:

at least partially enclosing the quantum-well sensor with a semiconductor material that has a different index of refraction so as to form a resonance optical cavity that has an optic axis parallel to the quantum-well layers; and making a resonant cavity mode of the optical cavity overlap with an absorption wavelength of the quantum-well sensor to increase an efficiency of absorption.

17. A method as in claim 16, wherein the overlap is achieved by adjusting at least one of the following: a configuration of the prism, the distance between the prism and the quantum-well sensor, a configuration of the quantum-well sensor, and the optical cavity.

18. A method as in claim 16, wherein the prism includes a third surface that is angled with respect to the second surface to couple radiation to the second surface.

19. A method as in claim 14, further comprising adjusting a relative orientation between a polarization of the beam incident to the prism and a direction of the prism to increase an amount of light that can be absorbed by the quantum-well sensor.

* * * * *